(12) United States Patent
Kim et al.

(10) Patent No.: US 12,128,255 B2
(45) Date of Patent: Oct. 29, 2024

(54) ULTRASONIC MEDICAL CARTRIDGE AND ULTRASONIC MEDICAL DEVICE INCLUDING THE SAME

(71) Applicant: JEISYS MEDICAL INC., Seoul (KR)

(72) Inventors: Kyun Tae Kim, Seoul (KR); Dong Hwan Kang, Seoul (KR)

(73) Assignee: Jeisys Medical Inc., Seoul (KR)

( * ) Notice: Subject to any disclaimer, the term of this patent is extended or adjusted under 35 U.S.C. 154(b) by 357 days.

(21) Appl. No.: 17/459,660

(22) Filed: Aug. 27, 2021

(65) Prior Publication Data

US 2022/0072337 A1  Mar. 10, 2022

(30) Foreign Application Priority Data

Sep. 9, 2020  (KR) .......................... 10-2020-0115236

(51) Int. Cl.
*A61B 5/05* (2021.01)
*A61N 7/00* (2006.01)

(52) U.S. Cl.
CPC ........ *A61N 7/00* (2013.01); *A61N 2007/0008* (2013.01)

(58) Field of Classification Search
CPC .......................... A61N 7/00; A61N 2007/0008
See application file for complete search history.

(56) References Cited

U.S. PATENT DOCUMENTS

| | | | |
|---|---|---|---|
| 5,331,861 A | 7/1994 | Joffe | |
| 5,511,438 A | 4/1996 | Aki | |
| 5,524,499 A | 6/1996 | Joffe | |
| 6,176,616 B1 | 1/2001 | Joffe | |
| 6,682,217 B1 | 1/2004 | Joffe | |
| 2001/0020398 A1 | 9/2001 | Erikson et al. | |
| 2003/0094056 A1 | 5/2003 | Park | |
| 2012/0197113 A1* | 8/2012 | Courtney | A61B 8/445 600/447 |
| 2014/0174224 A1 | 6/2014 | Zhang | |
| 2014/0184002 A1* | 7/2014 | Levin | H02K 7/08 310/90 |
| 2017/0028124 A1* | 2/2017 | Deak | A61M 5/1684 |
| 2017/0303888 A1* | 10/2017 | Jung | A61B 8/42 |
| 2020/0061394 A1 | 2/2020 | Yoo | |

FOREIGN PATENT DOCUMENTS

| | | |
|---|---|---|
| JP | 2015182521 A | 10/2015 |
| KR | 20120040909 A | 4/2012 |
| KR | 101487497 B1 | 1/2015 |
| KR | 10-1643885 B1 | 7/2016 |

(Continued)

OTHER PUBLICATIONS

Korean Intellectual Property Office, Notice of Office Action regarding Application No. 10-2020-0115236, Sep. 21, 2022.

(Continued)

*Primary Examiner* — Joel F Brutus
(74) *Attorney, Agent, or Firm* — Leydig, Voit & Mayer, Ltd.

(57) ABSTRACT

The inventive concept relates to an ultrasonic medical cartridge that may precisely move an ultrasonic wave generator by removing a backlash between a movable nut and a screw that move an ultrasonic wave generator, and an ultrasonic medical device including the same.

12 Claims, 4 Drawing Sheets

(56) References Cited

FOREIGN PATENT DOCUMENTS

| KR | 20190023842 A | 3/2019 |
| KR | 102117301 B1 | 6/2020 |
| KR | 20200085449 A | 7/2020 |

OTHER PUBLICATIONS

Korean Intellectual Property Office, Notice of Office Action regarding Application No. 10-2023-0044018, Nov. 20, 2023.
Japanese Patent Office, Notice of Reasons of Refusal regarding JP Application No. 2021-145984, Aug. 30, 2022.
Chinese Patent Office, The First Office Action regarding Application No. 202110988426.2, Dec. 29, 2003.
European Search Report regarding Application No. 21193191, filed Feb. 2, 2022.
Japanese Patent Office, Notice of Reasons of Refusal regarding JP Application No. 2023-070111, Apr. 16, 2024.

* cited by examiner

ULTRASONIC MEDICAL CARTRIDGE AND ULTRASONIC MEDICAL DEVICE INCLUDING THE SAME

CROSS-REFERENCE TO RELATED APPLICATIONS

A claim for priority under 35 U.S.C. § 119 is made to Korean Patent Application No. 10-2020-0115236 filed on Sep. 9, 2020 in the Korean Intellectual Property Office, the entire contents of which are hereby incorporated by reference.

BACKGROUND

Embodiments of the inventive concept described herein relate to an ultrasonic medical cartridge that may move an ultrasonic wave generator precisely by removing a backlash between a movable nut and a screw that move an ultrasonic wave generator in a lead screw manner, and an ultrasonic medical device including the same.

Recently, in the medical cosmetic field, in order to improve skin, for example, in order to remove fat, an ultrasonic medical device that may perform a skin improving procedure by using high-intensity focused ultrasound (HIFU) has been developed.

The ultrasonic medical device induces coagulation necrosis of fat cells by targeting focuses of high-intensity focused ultrasound generated by an ultrasonic wave generator to a target portion of a deep part of skin. The fat cells undergoing coagulation necrosis are naturally removed by a damage restoring mechanism of the human body.

Meanwhile, when the target portion of the deep part of the skin is changed, the ultrasonic wave generator has to be moved.

One of the manners for moving the ultrasonic wave generator is a lead screw manner.

The lead screw manner is a manner of moving the ultrasonic wave generator by a medium of a movable nut that is screw-coupled to the screw and is moved along a screw thread of the screw as the screw is rotated.

However, when the ultrasonic wave generator is moved in the existing lead screw manner, an error may be generated in a movement distance of the movable nut due to a backlash between the movable nut and the screw, and an error is also generated in a movement distance of the ultrasonic wave generator moved by a medium of the movable nut.

Accordingly, the existing lead screw manner has difficulty in precisely moving the ultrasonic wave generator.

Furthermore, according to the existing lead screw manner, when the ultrasonic wave generator is moved continuously or intermittently along a preset section, it is impossible to accurately align a movement starting point of the ultrasonic wave generator with a starting point of the preset section.

RELATED TECHNICAL DOCUMENT

[Patent Document]
(Patent document 1) Korean Patent No. 10-1643885 (Jul. 25, 2016)

SUMMARY

Embodiments of the inventive concept provide an ultrasonic medical cartridge that may precisely move an ultrasonic wave generator, and an ultrasonic medical device including the same.

The aspects of the inventive concept are not limited thereto, and other unmentioned aspects of the inventive concept may be clearly appreciated by those skilled in the art from the following descriptions According to an aspect of the inventive concept, an ultrasonic medical cartridge includes a cartridge housing, an ultrasonic wave generator accommodated in the cartridge housing, a movement unit including a movable nut coupled to the ultrasonic wave generator and a screw screw-coupled to the movable nut, and configured such that the movable nut is moved along the screw when the screw is rotated, and a pressing unit that applies pressure to the movable nut such that the movable nut and the screw are adhered to each other.

Furthermore, the pressing unit may include a first magnetic member located at one end of the movable nut, which is adjacent to the screw, and a second magnetic member disposed to be spaced apart from the first magnetic member in a movement direction of the movable nut.

Furthermore, the pressure may be applied to the movable nut by a mutual repulsive force of the first magnetic member and the second magnetic member.

Furthermore, the first magnetic member and the second magnetic member may be formed in a shape corresponding to each other.

According to another aspect of the inventive concept, an ultrasonic medical device may include a handpiece, a cartridge housing coupled to the handpiece to be separable, an ultrasonic wave generator accommodated in the cartridge housing, a movement unit including a movable nut coupled to the ultrasonic wave generator and a screw screw-coupled to the movable nut, and configured such that the movable nut is moved along the screw when the screw is rotated, and a pressing unit that applies pressure to the movable nut such that the movable nut and the screw are adhered to each other.

Furthermore, the pressing unit includes a first magnetic member located at one end of the movable nut, which is adjacent to the screw, and a second magnetic member disposed to be spaced apart from the first magnetic member in a movement direction of the movable nut.

Furthermore, the pressure may be applied to the movable nut by a mutual repulsive force of the first magnetic member and the second magnetic member.

Furthermore, the ultrasonic medical device may further include a driving device accommodated in the handpiece and that rotates the screw, and a coupler connecting a driving shaft of the driving device and the screw, and the second magnetic member may be coupled to a facing surface of the coupler, which faces the first magnetic member.

According to another aspect of the inventive concept, a backlash preventing device includes a movement unit including a movable nut and a screw screw-coupled to the movable nut, and configured such that the movable nut is moved along the screw when the screw is rotated, and a pressing unit that applies pressure to the movable nut such that the movable nut and the screw are adhered to each other.

Furthermore, the pressing unit may include a first magnetic member located at one end of the movable nut, which is adjacent to the screw, and a second magnetic member disposed to be spaced apart from the first magnetic member in a movement direction of the movable nut.

Furthermore, the pressure may be applied to the movable nut by a mutual repulsive force of the first magnetic member and the second magnetic member.

The other detailed items of the inventive concept are included in the detailed description of the inventive concept and the drawings.

DETAILED DESCRIPTION

Figure 1:
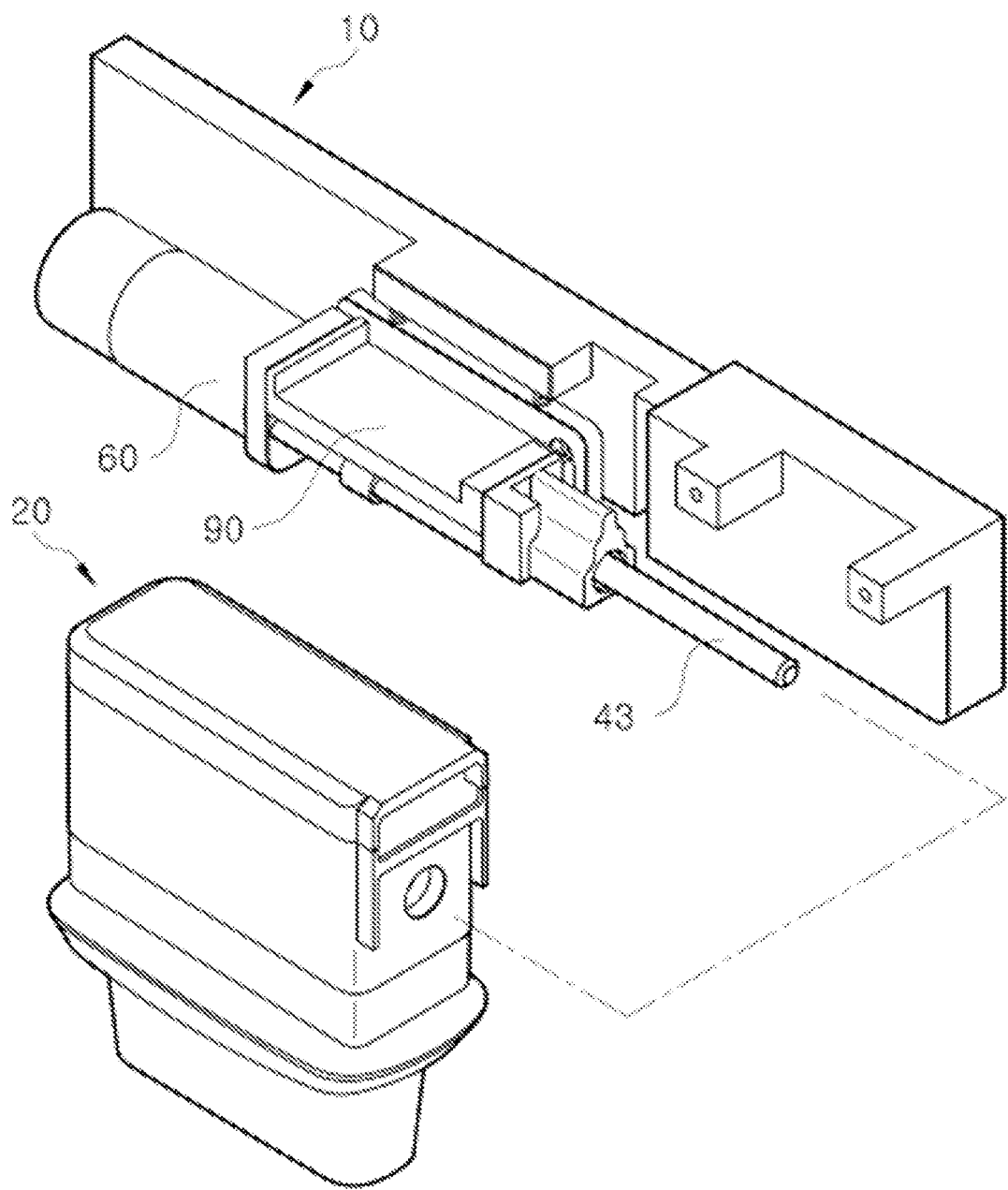
FIG. 1 is a perspective view illustrating a state, in which a cartridge housing and a handpiece of an ultrasonic medical device are separated, according to an embodiment of the inventive concept.

The above and other aspects, features, and advantages of the inventive concept will become apparent from the following description of the following embodiments given in conjunction with the accompanying drawings. However, the inventive concept is not limited by the embodiments disclosed herein but will be realized in various different forms, and the embodiments are provided only to make the disclosure of the inventive concept complete and fully inform the scope of the inventive concept to an ordinary person in the art, to which the inventive concept pertains, and the inventive concept will be defined by the scope of the claims.

The terms used herein are provided to describe the embodiments but not to limit the inventive concept. In the specification, the singular forms include plural forms unless particularly mentioned. The terms "comprises" and/or "comprising" used herein does not exclude presence or addition of one or more other elements, in addition to the aforementioned elements. Throughout the specification, the same reference numerals denote the same elements, and "and/or" includes the respective elements and all combinations of the elements. Although "first", "second" and the like are used to describe various elements, the elements are not limited by the terms. The terms are used simply to distinguish one element from other elements. Accordingly, it is apparent that a first element mentioned in the following may be a second element without departing from the spirit of the inventive concept.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

The terms, such as "below", "beneath", "lower", "above", and "upper", which are spatially relative may be used to easily describe a correlation between one element and other elements as illustrated in the drawings. The spatially relative terms have to be understood as terms including different directions of the elements during use or an operation, in addition to the direction illustrated in the drawings. For example, when the elements illustrated in the drawings are overturned, the elements "below" or "beneath" another element may be positioned "above" the other element. Accordingly, the term "below" or "beneath" may include "below" or "beneath" and "above". The element may be oriented in different directions, and accordingly, the spatially relative terms may be construed according to the orientation.

Hereinafter, exemplary embodiments of the inventive concept will be described in detail with reference to the accompanying drawings.

Figure 2:
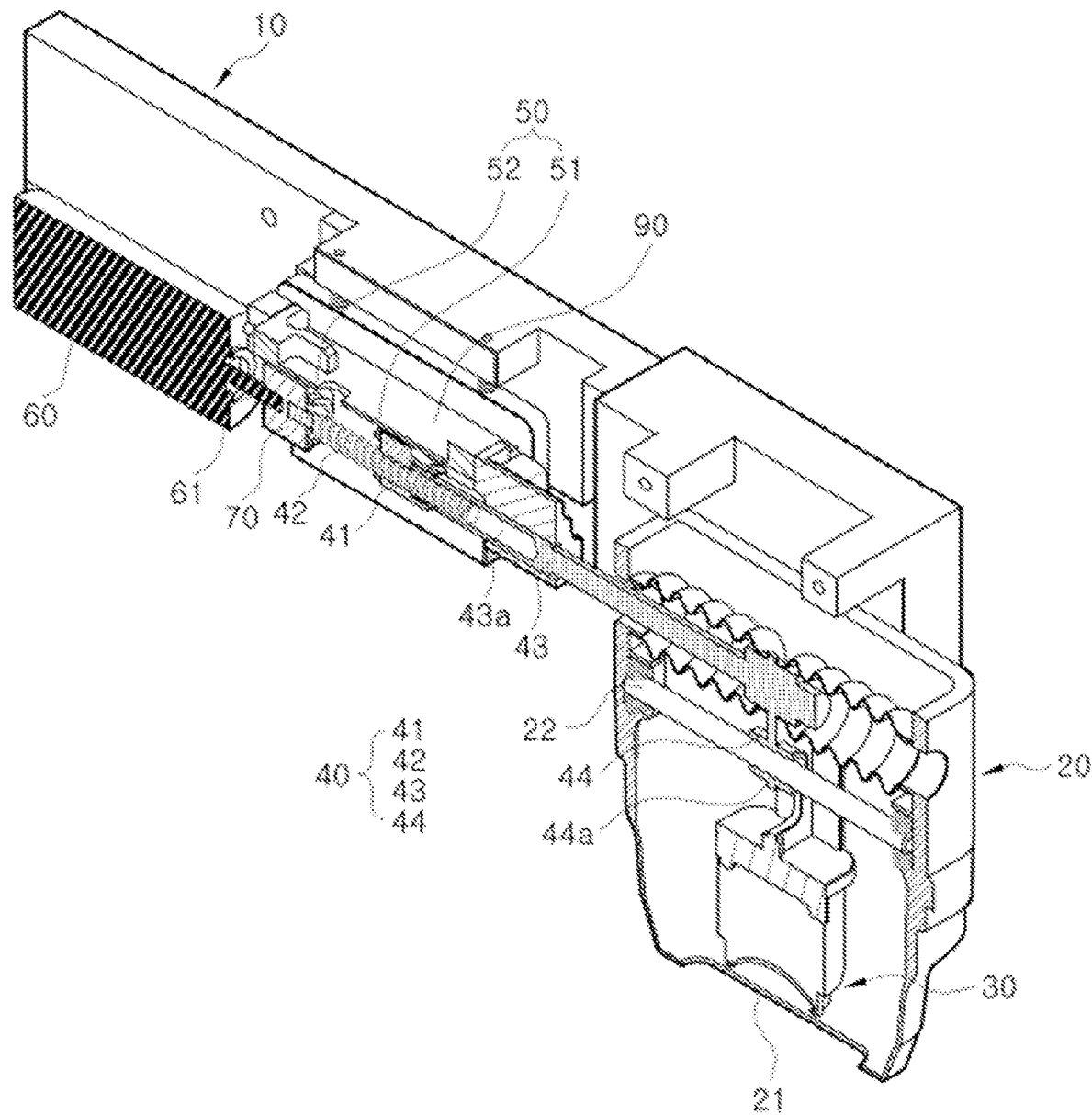
FIG. 2 is a cutaway view illustrating an ultrasonic medical device according to an embodiment of the inventive concept, which is cut in a vertical direction.
Figure 3:
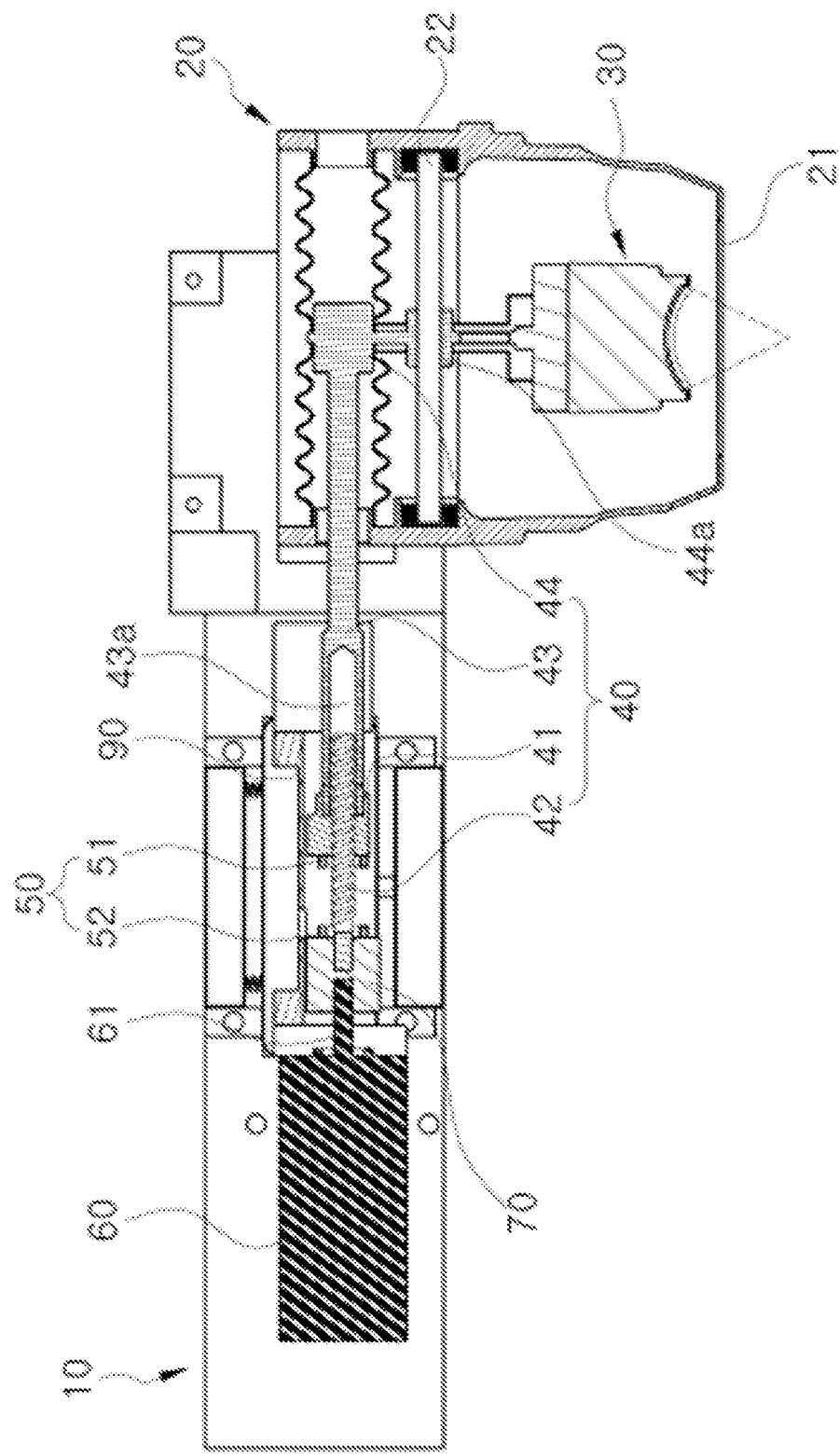
FIG. 3 is a cross-sectional view illustrating an ultrasonic medical device according to an embodiment of the inventive concept.

FIG. 1 is a perspective view illustrating a state, in which a cartridge housing and a handpiece of an ultrasonic medical device are separated, according to an embodiment of the inventive concept. FIG. 2 is a cutaway view illustrating an ultrasonic medical device according to an embodiment of the inventive concept, which is cut in a vertical direction. FIG. 3 is a cross-sectional view illustrating an ultrasonic medical device according to an embodiment of the inventive concept.

As illustrated in FIGS. 1 to 3, an ultrasonic medical device according to an embodiment of the inventive concept includes a handpiece 10, a cartridge housing 20, an ultrasonic wave generator 30, a movement unit 40, and a pressing unit 50.

The handpiece 10 is a basic body, and may be utilized as a knob that is gripped by a user, and the cartridge housing 20, in which the ultrasonic wave generator 30 is accommodated, may be coupled to one side of the handpiece 10 to be separable.

Accordingly, an ultrasonic medical procedure may be performed in a manner, in which high-intensity focused ultrasound generated by the ultrasonic wave generator 30 are irradiated to a specific depth of a deep part of skin in a state, in which the user grips the handpiece 10 and moves the handpiece 10 such that the cartridge housing 20 is adhered to a surface of the skin.

An interior of the handpiece 10 may be provided with a driving device 60 and an RF board that applies an RF current to the ultrasonic wave generator 30. The RF board may intermittently or continuously apply the RF current to the driving device 60 and the ultrasonic wave generator 30.

The cartridge housing 20 is a kind of a case that accommodates the ultrasonic wave generator 30, and is installed on one side of the handpiece 10 to be separable.

A deairing liquid that is a medium of high-intensity focused ultrasound generated by the ultrasonic wave generator 30 may be accommodated in an interior of the cartridge housing 20. For example, the deairing liquid may be moisture, from which gases are removed, but is not specifically limited thereto.

A transmission window 21 that transmits high-intensity focused ultrasound generated by the ultrasonic wave generator 30 may be provided at a distal end of the cartridge housing 20. For example, the transmission window 21 may be an ultrasonic wave transmitting film that transmits high-intensity focused ultrasound, but is not specifically limited thereto.

The ultrasonic wave generator 30 may be a transducer that is accommodated in the cartridge housing 20 and generates high-intensity focused ultrasound. The transducer may receive the RF current from the RF board of the handpiece 10 and generate the high-intensity focused ultrasound. Then, the high-intensity focused ultrasound generated by the ultrasonic wave generator 30 may be irradiated to the specific depth of the deep part of the skin while transmitting through the transmission window 21 at the distal end of the cartridge housing 20.

The ultrasonic wave generator 30 is moved by a medium of a movable nut 41 that is screw-coupled to the screw 42 and is moved along the screw 42 as the screw 42 is rotated. Then, as the movable nut 41 and the ultrasonic wave generator 30 are integrally coupled to each other, the movable nut 41 and the ultrasonic wave generator 30 may be integrally moved, and in this way, a manner for moving the ultrasonic wave generator 30 may be defined as a lead-screw manner.

The movement unit 40 is adapted to move the ultrasonic wave generator 30, and includes the movable nut 41 integrally coupled to the ultrasonic wave generator 30, and the screw 42 screw-coupled to the movable nut 41 and rotated by the driving device 60.

As a screw thread is formed on an inner peripheral surface of the movable nut 41 and a screw thread is formed on an outer peripheral surface of the screw 42 along a lengthwise direction thereof, the movable nut 41 and the screw 42 may be screw-coupled to each other.

Accordingly, when the screw 42 is rotated, the movable nut 41 may be moved in the lengthwise direction of the screw 42 along the screw thread of the screw 42.

As an example, the movable nut 41 may be moved from one lengthwise end to an opposite lengthwise end of the screw 42 when the screw 42 is rotated in one direction, and the movable nut 41 may be moved from the opposite lengthwise end to the one lengthwise end of the screw 42 when the screw 42 is rotated in an opposite direction.

As another example, the movable nut 41 may be moved from the opposite lengthwise end to the one lengthwise end of the screw 42 when the screw 42 is rotated in the one direction, and the movable nut 41 may be moved from the one lengthwise end to the opposite lengthwise end of the screw 42 when the screw 42 is rotated in the opposite direction.

That is, the movement direction of the movable nut 41 may be the lengthwise direction of the screw 42, and in more detail, the movement direction of the movable nut 41 may include a direction that faces the opposite lengthwise end of the screw 42 from the one lengthwise end of the screw 42, and a direction that faces the one lengthwise direction of the screw 42 from the opposite lengthwise direction of the screw 42.

Moreover, when a disposition direction of the screw 42 is a horizontal direction, the movement direction of the movable nut 41 becomes the horizontal direction, and when the disposition direction of the screw 42 is a vertical direction, the movement direction of the movable nut 41 becomes the vertical direction. However, the vertical direction and the horizontal direction are not limited to the meanings of geometric vertical and horizontal directions, and the vertical direction may be defined as an upward/downward direction with respect to the drawings and the horizontal direction may be defined as a leftward/rightward direction with respect to the drawings. Furthermore, the horizontal direction is defined as a direction that is perpendicular to the vertical direction, but is not defined as being strictly geometrically perpendicular to the vertical direction. In other words, when a direction is viewed as being closer to the direction that is perpendicular to the horizontal direction than the horizontal direction, it should be understood as being perpendicular.

The screw 42 and the movable nut 41 may be accommodated in the handpiece 10, and a movable shaft 43 and a support shaft 44 may be installed between the movable nut 41 and the ultrasonic wave generator 30.

The movable shaft 43 and the support shaft 44 connect the movable nut 41 and the ultrasonic wave generator 30, and the movable shaft 43 may be accommodated in the handpiece 10 and the support shaft 44 may be accommodated in the cartridge housing 20.

The movable shaft 43 functions to connect the movable nut 41 and the support shaft 44. The opposite end of the movable shaft 43 is integrally coupled to the movable nut 41. One end of the movable shaft 43 may be disposed to protrude from the handpiece 10, and may be accommodated in the cartridge housing 20 when the handpiece 10 and the cartridge housing 20 are fastened.

The movable shaft 43 may have a hollow part 43a that is hollow in a lengthwise direction thereof from one end thereof, which is integrally coupled to the movable nut 41. The screw 42 may be inserted into the hollow part 43a, and the hollow part 43a may have a diameter that is larger than that of the screw 42 to prevent interference with the screw 42 when the screw 42 is inserted or rotated.

The support shaft 44 functions to connect the movable shaft 43 and the ultrasonic wave generator 30. One end of the support shaft 44 is coupled to the opposite end of the movable shaft 43 to be separable. For example, the opposite end of the movable shaft 43 may pass through the one end of the support shaft 44 to be fixed. Meanwhile, an opposite end of the support shaft 44 is coupled to the ultrasonic wave generator 30.

Moreover, when the movable nut 41 is moved along the screw 42 as the screw 42 is rotated, the movable nut 41, the movable shaft 43, the support shaft 44, and the ultrasonic wave generator 30 may be integrally moved in a movement direction of the movable nut 41.

A guide shaft 22 that is disposed in parallel to the movable shaft 43 may be accommodated in the cartridge housing 20, and a mounter 44a that is mounted to be slid along the guide shaft 22 may be formed in the support shaft 44. Opposite ends of the guide shaft 22 may be elastically supported by an elastic member. Here, the elastic member may be a compression spring, but is not specifically limited thereto.

The pressing unit 50 removes a backlash between the movable nut 41 and the screw 42 by applying pressure to the movable nut 41 such that the movable nut 41 and the screw 42 are adhered to each other.

Accordingly, according to the ultrasonic medical device according to the embodiment of the inventive concept, the ultrasonic wave generator 30 may be precisely moved by removing a backlash between the movable nut 41 and the screw 42 of the movement unit 40 that moves the ultrasonic wave generator 30 in the lead screw manner with the pressing unit 50.

Moreover, according to the ultrasonic medical device according to the embodiment of the inventive concept, because the ultrasonic wave generator 30 may be precisely moved, a movement starting point of the ultrasonic wave generator 30 is precisely aligned with a starting point in a preset section even when the ultrasonic wave generator 30 is continuously moved or intermittently moved along the preset section. As a result, the ultrasonic wave generator 30 may be precisely moved from the starting point of the preset section along the final point of the preset section.

The driving device 60 is provided in the handpiece 10, and functions to rotate the screw 42. The driving device 60 may receive an RF current from the RF board of the handpiece 10 and rotate the screw 42. As an example, the driving device 60 may be a reversible motor, a hydraulic motor, a pneumatic motor, and the like, but is not specifically limited thereto.

A driving shaft 61 of the driving device 60 may be connected the screw 42 by a medium of a coupler 70. That is, the coupler 70 functions to connect the driving shaft 61 of the driving device 60 and the screw 42.

The locations of the driving device 60 and the movement unit 40, in a locations of the driving device 60 and the movement unit 40, in a direction that is perpendicular to the movement direction of the movable nut 41, may be adjusted by an adjustment unit (not illustrated). Here, the movable shaft 43 and the driving device 60 is supported by a movable plate 90 installed in the interior of the handpiece 10 to be movable, and the movable plate 90 is installed in the interior of the handpiece 10 to be movable in a direction that is perpendicular to the movement direction of the movable nut 41.

The adjustment unit (not illustrated) may move the movable plate 90 in the direction that is perpendicular to the movement direction of the movable nut 41, and accordingly, the driving device 60 and the movement unit 40 fixed to the movable plate 90 may be moved in the direction that is perpendicular to the movement direction of the movable nut 41.

As an example, the adjustment unit (not illustrated) includes an outer rotor (not illustrated), and an inner rotor (not illustrated), one side of which supports the movable plate 90 and an opposite side of which is installed in an interior of the outer rotor (not illustrated), a protruding length of the inner rotor (not illustrated) from the outer rotor (not illustrated) to the movable plate 90 may be adjusted through rotation of the outer rotor (not illustrated), and in this way, the movable plate 90 may be moved in the direction that is perpendicular to the movement direction of the movable nut 41 by adjusting a protruding length of the inner rotor (not illustrated) from the outer rotor (not illustrated).

Figure 4:
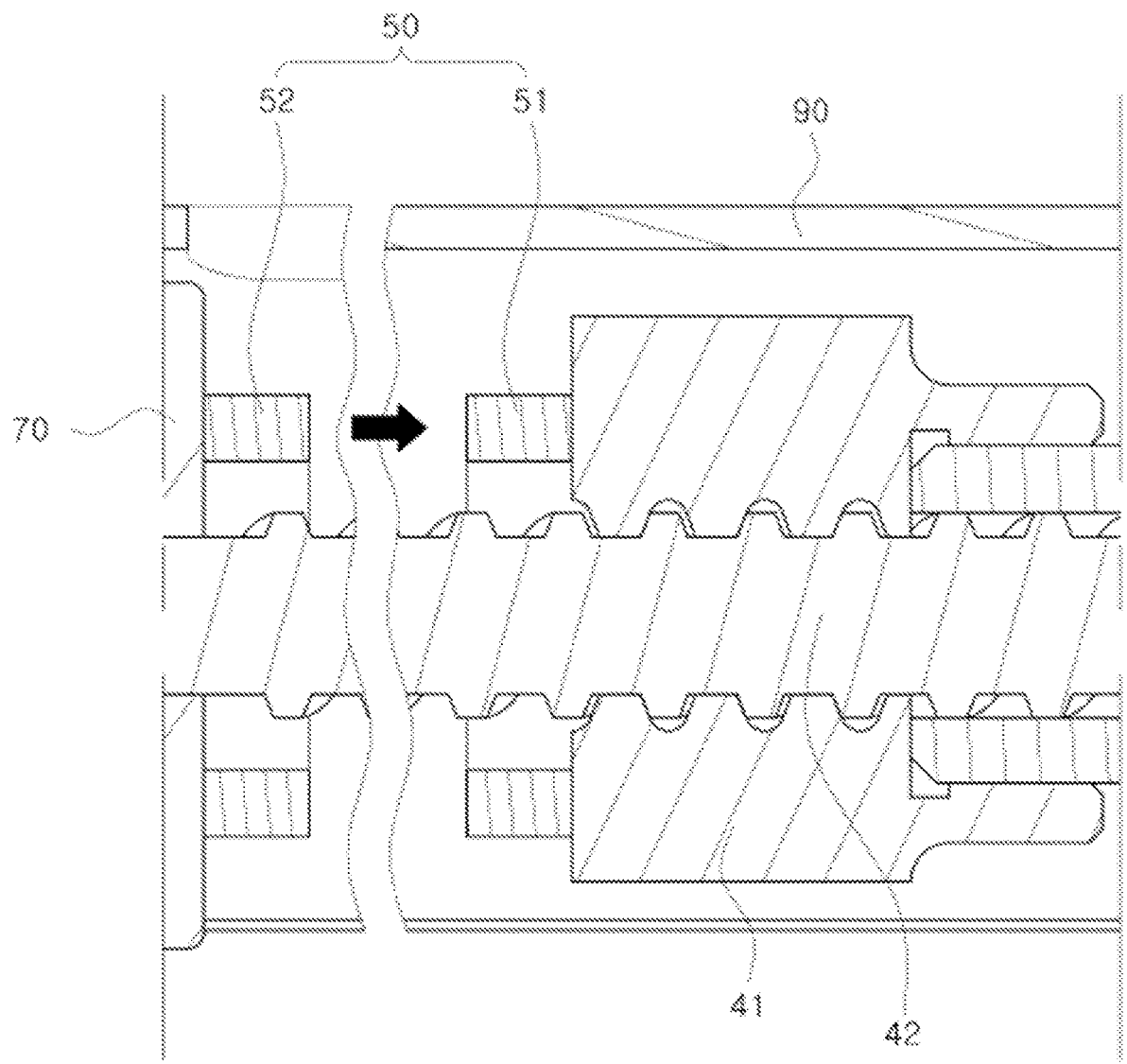
FIG. 4 is an enlarged view illustrating a first magnetic member and a second magnetic member of an ultrasonic medical device according to an embodiment of the inventive concept.

FIG. 4 is an enlarged view illustrating a first magnetic member and a second magnetic member of an ultrasonic medical instrument according to an embodiment of the inventive concept.

As illustrated in FIGS. 1 to 4, the pressing unit 50 may include a first magnetic member 51 and a second magnetic member 52.

The first magnetic member 51 is coupled to one end of the movable nut 41, which is adjacent to the screw 42, and the second magnetic member 52 is disposed to be spaced apart from the first magnetic member 51 in the movement direction of the movable nut 41. Here, the second magnetic member 52 may be installed on a surface of the coupler 70, which faces the first magnetic member 51.

The first magnetic member 51 and the second magnetic member 52 may have the same polarity as each other.

Accordingly, a mutual repulsive force may be generated between the first magnetic member 51 and the second magnetic member 52, and accordingly, the movable nut 41 is pressed as the second magnetic member 52 coupled to the movable nut 41 is pushed in the movement direction of the movable nut 41 (that is, a direction that becomes farther from the first magnetic member 51). As a result, as the movable nut 41 and the screw 42 are coupled to each other, a backlash between the movable nut 41 and the screw 42 is removed.

The first magnetic member 51 and the second magnetic member 52 may be formed in a shape corresponding to each other. For example, the first magnetic member 51 and the second magnetic member 52 may have corresponding annular shapes having an inner diameter and an outer diameter. This is because a magnetic force applied to the second magnetic member 52 by the first magnetic member 51 may be stably maintained even when the first magnetic member 51 is rotated. Moreover, the first magnetic member 51 and the second magnetic member 52 may have polygonal shapes, but are not specifically limited thereto. Furthermore, a single first magnetic member 51 and a single second magnetic member 52 may be provided or a plurality of first magnetic members 51 and a plurality of second magnetic members 52 may be arranged along a circumferential direction.

The first magnetic member 51 and the second magnetic member 52 may be disposed at the same height as each other. In detail, the first magnetic member 51 and the second magnetic member 52 may be disposed such that the inner diameters and the outer diameters thereof are at the same heights as each other.

Further, all of a central axis of the first magnetic member 51, a central axis of the second magnetic member 52, and a central axis of the driving shaft 61 of the driving motor may be arranged in a row.

As a result, because a height, at which a mutual repulsive force is applied between the first magnetic member 51 and the second magnetic member 52, is maintained even when the first magnetic member 51 is rotated, the movable nut 41, to which pressure is applied by the mutual repulsive force of the first magnetic member 51 and the second magnetic member 52, may be prevented from being biased.

As an example, the first magnetic member 51 and the second magnetic member 52 may be permanent magnets. In this case, because the first magnetic member 51 and the second magnetic member 52 do not require separate supply of electric power, power consumptions may be reduced.

As an example, the first magnetic member 51 and the second magnetic member 52 may be electromagnets. In this case, the first magnetic member 51 and the second magnetic member 52 may receive the RF current from the RF board of the handpiece 10.

Meanwhile, the handpiece 10 of the inventive concept may include a sensor (not illustrated). The sensor (not illustrated) may sense a movement of the movement unit 40, and, for example, may be a Hall sensor or a photo sensor, but is not specifically limited thereto.

Meanwhile, the cartridge housing 20 of the inventive concept may also accommodate a sensor (not illustrated). The sensor (not illustrated) may sense a movement of the ultrasonic wave generator 30, and, for example, may be a Hall sensor or a photo sensor, but is not specifically limited thereto.

Meanwhile, because the cartridge housing 20, the ultrasonic wave generator 30, the movement unit 40, and the pressing unit 50 included the ultrasonic medical cartridge according to the embodiment of the inventive concept are the same as the cartridge housing 20, the ultrasonic wave generator 30, the movement unit 40, and the pressing unit 50 included the ultrasonic medical device according to the embodiment of the inventive concept, a detailed description thereof will be omitted.

Accordingly, according to the ultrasonic medical cartridge and the ultrasonic medical device including the same according to the embodiment of the inventive concept, the ultrasonic wave generator may be precisely moved by removing a backlash between the movable nut and the screw of the movement unit that moves the ultrasonic wave generator in the lead screw manner with the pressing unit.

The effects of the inventive concept are not limited thereto, and other unmentioned effects of the inventive concept may be clearly appreciated by those skilled in the art from the following descriptions.

Although the exemplary embodiments of the inventive concept have been described with reference to the accompanying drawings, it will be understood by those skilled in the art to which the inventive concept pertains that the inventive concept can be carried out in other detailed forms without changing the technical spirits and essential features thereof. Therefore, the above-described embodiments are exemplary in all aspects, and should be construed not to be restrictive.

What is claimed is:

1. An ultrasonic medical cartridge, comprising:
a cartridge housing;
an ultrasonic wave generator accommodated in the cartridge housing;
a movable nut coupled to the ultrasonic wave generator;
a screw screw-coupled to the movable nut, such that the movable nut is configured to be moved along the screw when the screw is rotated; and
a first magnetic member located at one end of the movable nut, wherein the first magnetic member is configured to apply pressure to the movable nut such that the movable nut and the screw are adhered to each other based on the first magnetic member being repulsed by a second magnetic member having the same polarity as the first magnetic member disposed on an apparatus coupled to the screw.

2. The ultrasonic medical cartridge of claim 1, wherein the first magnetic member and the second magnetic member are formed in shapes corresponding to each other.

3. The ultrasonic medical cartridge of claim 2, wherein the first and second magnetic members have annular shapes.

4. The ultrasonic medical cartridge of claim 2, wherein the first and second magnetic members have polygonal shapes.

5. An ultrasonic medical device, comprising:
a handpiece;
a cartridge housing couplable to and separable from the handpiece;
an ultrasonic wave generator accommodated in the cartridge housing;
a movable nut coupled to the ultrasonic wave generator;
a screw screw-coupled to the movable nut, such that the movable nut is configured to be moved along the screw when the screw is rotated;
a driving device accommodated in the handpiece, wherein the driving device is configured to rotate the screw;
a coupler connecting a driving shaft of the driving device and the screw;
a first magnetic member located at one end of the movable nut; and
a second magnetic member coupled to a surface of the coupler;
wherein the first magnetic member and the second magnetic member have the same polarity and are configured to repel each other to apply pressure to the movable nut such that the movable nut and the screw are adhered to each other.

6. The ultrasonic medical device of claim 5, wherein the first magnetic member and the second magnetic member are formed in shapes corresponding to each other.

7. The ultrasonic medical device of claim 6, wherein the first and second magnetic members have annular shapes.

8. The ultrasonic medical device of claim 6, wherein the first and second magnetic members have polygonal shapes.

9. A backlash preventing system for an ultrasonic medical device, comprising:
a movable nut coupled to an ultrasonic wave generator of the ultrasonic medical device;
a screw screw-coupled to the movable nut, such that the movable nut is configured to be moved along the screw when the screw is rotated;
a coupler connecting the screw and a driving shaft of a driving device of the ultrasonic medical device;
a first magnetic member located at one end of the movable nut; and
a second magnetic member coupled to a surface of the coupler;
wherein the first magnetic member and the second magnetic member have the same polarity and are configured to repel each other to apply pressure to the movable nut such that the movable nut and the screw are adhered to each other.

10. The backlash preventing system of claim 9, wherein the first magnetic member and the second magnetic member are formed in shapes corresponding to each other.

11. The backlash preventing system of claim 10, wherein the first and second magnetic members have annular shapes.

12. The backlash preventing system of claim 10, wherein the first and second magnetic members have polygonal shapes.

* * * * *